United States Patent [19]

Dobson et al.

[11] 4,182,667
[45] Jan. 8, 1980

[54] ION-SENSITIVE ELECTRODES

[75] Inventors: John V. Dobson, Hartlepool; Thomas Dickinson, Newcastle-upon-Tyne, both of England

[73] Assignee: National Research Development Corporation, London, England

[21] Appl. No.: 908,441

[22] Filed: May 22, 1978

Related U.S. Application Data

[60] Division of Ser. No. 741,494, Nov. 12, 1976, Pat. No. 4,111,777, which is a continuation of Ser. No. 605,881, Aug. 19, 1975, abandoned.

[30] Foreign Application Priority Data

Sep. 4, 1974 [GB] United Kingdom ............... 38748/74

[51] Int. Cl.² ...................... G01N 27/30; G01N 27/58
[52] U.S. Cl. .............................. 204/195 M; 204/1 T; 204/195 S
[58] Field of Search ............... 204/1 T, 1 Y, 1 P, 1 S, 204/1 B, 1 N, 1 K, 1 F, 1 A, 1 H, 195 H, 195 M, 195 S; 429/104

[56] References Cited

U.S. PATENT DOCUMENTS

| 3,881,955 | 5/1975 | Dubin et al. ..................... 429/104 X |
| 3,882,012 | 5/1975 | Dickinson et al. ............... 204/195 P |

OTHER PUBLICATIONS

Limin Hseuh et al., J. Electrochem. Soc., pp. 1128–1130, Jul. 1971.
B. V. Joglekar et al., Canadian Metallurgical Quaterly, vol. 12, No. 2, pp. 155–158, (1973).
J. M. Thomas et al., J. Materials Science, No. 7, pp. 838–840, (1972).

Primary Examiner—G. L. Kaplan
Attorney, Agent, or Firm—Cushman, Darby & Cushman

[57] ABSTRACT

Ion-sensitive electrodes are described for determining the concentration of cations of a predetermined type in electrolytes. In one such electrode a material with a high ionic mobility such as a β alumina may be used to protect material, such as a mercury amalgam, which allows interactions requiring the supply of electrons and the cations to take place internally, both materials containing cations of the predetermined type.

2 Claims, 4 Drawing Figures

ION-SENSITIVE ELECTRODES

CROSS-REFERENCE TO RELATED APPLICATION

This application is a division of our application Ser. No. 741,494 filed Nov. 12, 1976, now U.S. Pat. No. 4,111,777, which, in turn, is a continuation of application Ser. No. 605,881 filed Aug. 19, 1975, now abandoned.

BACKGROUND OF THE INVENTION

The present invention relates to ion-sensitive electrodes for determining the concentrations of certain mainly cations in electrolytes.

Known ion-senstive electrodes for monovalent cations have several disadvantages; erosion by electrolytes in which the electrodes are placed tends to occur, the maximum temperature at which such electrodes can be used is the boiling point of water and since the electrodes often take the form of glass electrodes with an internal electrolyte they are relatively fragile. In addition known ion-sensitive electrodes sensitive to monovalent cations tend to be unstable with time and temperature. Further the concentrations of certain monovalent cations such as $Rb^+$, $Cs^+$ and $Li^+$ could not formerly be measured at all by electro-analytical techniques using ion-sensitive electrodes. It is expected that at least some of the above disadvantages will be wholly or partly overcome by the present invention.

DETAILED DESCRIPTION OF THE INVENTION

According to a first aspect of the present invention there is provided an ion-sensitive electrode for determining the concentration of selected cations other than proton in at least one electrolyte, comprising a member which includes a material of non-stoichiometric composition, having a high ionic mobility, containing cations of the type whose concentration is to be determined, and having a structure which allows interactions requiring electrons and cations of the said type to take place at the electrode surface and/or within the material, and means for making electrical contact with the member.

The said member may have a crystal lattice structure with a spatial configuration which allows ion transfer to take place and also gives the material a high ionic mobility.

According to a second aspect of the present invention there is provided an ion-sensitive electrode for determining the concentration of selected cations in at least one electrolyte, comprising a first member which includes a first material having a high ionic mobility and which contains cations of the type whose concentration is to be determined, the first material not being capable of substantial chemical reaction with at least one electrolyte, a second member in contact with the first member, which includes an electrically conductive second material which also contains cations of the said type and which allows interactions requiring the supply of electrons and the said cations to take place internally, and/or at the interface between the first and second members, and means for making electrical contact with the second material, the electrode being so constructed that the second member, but not the first is isolated in operation from electrolytes.

Electrodes according to the second aspect of the invention are primarily for use where the second material reacts chemically with the said electrolyte.

Cations whose concentration may be determined by using electrodes in accordance with the first or second aspects of the invention include: $Na^+$, $K^+$, $Rb^+$, $Li^+$, $Tl^+$, $Ag^+$, $Cu^+$, $NO^+$, $Cs^+$, and $NH_4^+$. Thus it can be seen that a wide range of ion-sensitive electrodes according to the invention is available and this range includes electrodes for some ions which previously could not be measured by electro-analytical techniques.

In electrodes in accordance with the first aspect of the invention the non-stoichiometric material may be a tungsten bronze such as sodium tungsten bronze, $Na_x WO_3$ where x varies from just above 0 to 1, or another inorganic bronze which has a spatial configuration allowing transfer of the ion of interest; for example a titanium, vanadium or molybdenum bronze.

The second material of the second aspect of the invention may also be a non-stoichiometric material such as one of the bronzes mentioned above.

The $Na^+$ cation in sodium tungsten bronze may be replaced wholly or partly with $K^+$, $Li^+$, and $NH_4^+$ and the resulting material ($Na_x M_y WO_3$ where M represents $K^+$ or $Li^+$ or $NH_4^+$ and y varies from just above 0 to 1 and x plus y must not be greater than 1) then behaves reversably to the substituted cation and may be used as the non-stoichiometric material in electrodes according to the first and second aspects of the invention. Methods of preparing the above-mentioned tungsten bronzes are described in "Fast Ion Transport in Solids" edited by Van Gool (1973) published by North Holland, and such methods may also be found in the Quarterly Review, 22, 30 (1968).

In the second aspect of the invention the first material may be a β alumina containing cations of the said type and the second material may be a mercury amalgam also containing cations of the selected type.

A common β alumina is sodium β alumina whose formula is nominally given as $Na Al_{11} O_{17}$. Substitution for cations other than $Na^+$ can readily be achieved for $Li^+$, $K^+$, $Rb^+$, $Ag^+$, $Tl^+$, $NH_4^+$ and $In^+$ and is described in the Journal of Inorganic Nuclear Chemistry 29, 2453 (1967). Similar substitutions are described for $NO^+$ in Inorganic Chemistry 8, 2531 (1969); for $Ga^+$ in Inorganic Chemistry 8,994 (1969); and for $Cu^+$ in U.S. Government Research and Development Report 16 No; AD 693,158, (1969) M. S. Whittingham, R. W. Helliwell and R. A. Huggins.

It will therefore be seen that ion-sensitive electrodes according to the invention may be constructed from solid materials and for this reason are less fragile than many known electrodes which have internal electrolytes and can be used at much higher temperatures, at least up to 200° C. The specified materials are more chemically durable than those used in many known ion-sensitive electrodes. Since electrodes according to the invention may be constructed with a relatively low electrical resistance, they are easily used with conventional potential measuring equipment for ion-sensitive electrodes.

In a preferred ion-sensitive electrode according to the second aspect of the invention the first member includes β alumina, the second member includes solid mercury amalgam, the means for making electrical contact with the second material includes a platinum contact means, and both the β alumina and mercury amalgam contain cations of the type which it is desired to detect.

In a further preferred electrode according to the second aspect of the invention the first member includes β alumina, and the second member includes a tungsten bronze.

Of the two preferred electrodes the former is useful in aqueous electrolytes which would react with the mercury amalgam if it were not for the β alumina member; and the second preferred electrode is useful for media which might attack tungsten bronze.

BRIEF DESCRIPTION OF THE DRAWINGS

Certain embodiments of the invention will now be described, by way of example, with reference to the accompanying drawings, in which.

DETAILED DESCRIPTION OF THE DRAWINGS

Figure 1:
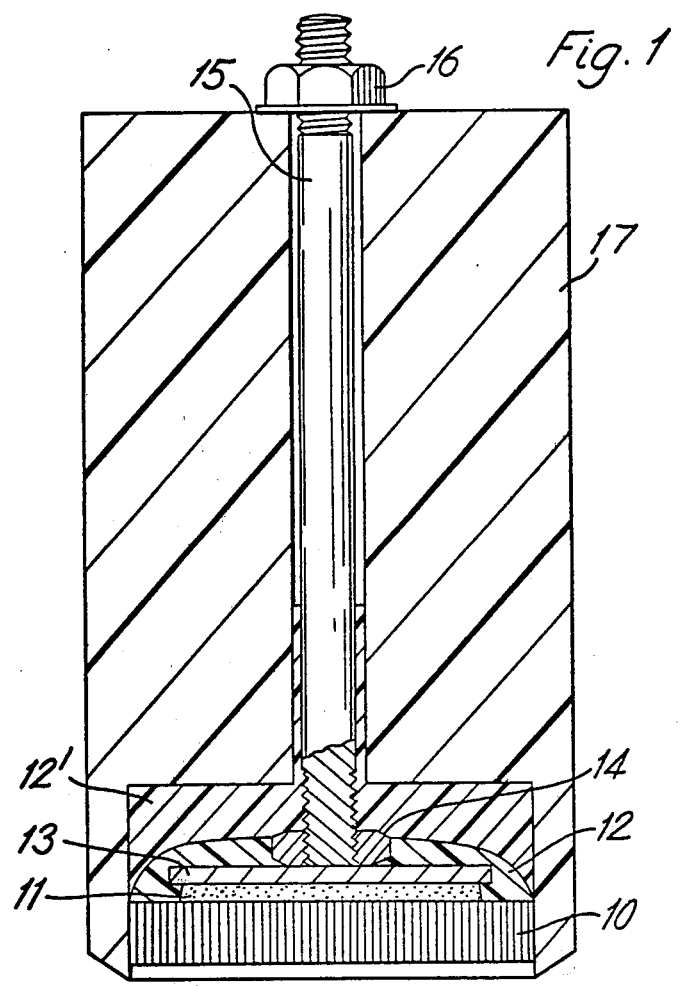
FIG. 1 is a cross-section through a first embodiment of the invention including a β alumina member protecting a mercury amalgam member.

In FIG. 1 a sodium β alumina disc 10 is held in contact with sodium-mercury amalgam 11 by a surrounding casing of araldite 12. The amalgam is also in contact with a platinum disc 13 fixed by araldite to a brass nut 14 in electrical contact with the platinum. When the araldite 12 has been cured, a length of brass studding 15 is screwed to the nut 14 and also to another nut 15 which holds the electrode assembly to the PTFE body 17 and acts as the electrical connection to the electrode. At the same time additional araldite 12' is added to ensure that electrolyte is prevented from reaching the nut 14 or the studding 15 and this additional araldite is then cured.

The solid sodium mercury amalgam is made by drying a small chip of metallic sodium with filter papers and depositing the chip in a small glass vessel which already contains a small amount of dry clean mercury. The glass vessel is shaken and a spontaneous reaction takes place. If, after visible reaction has ceased, the resultant mass is not solid more chips of sodium are added until a solid but pliable amalgam is formed. Other amalgams are made using the same method but substituting a metal whose ions are not to be detected for the sodium.

Before use the electrode is conditioned in a neutral solution of the ion to be detected; for example in this the active part of the electrode is immersed in say 0.1 M NaCl for 24 hours.

Figure 4:
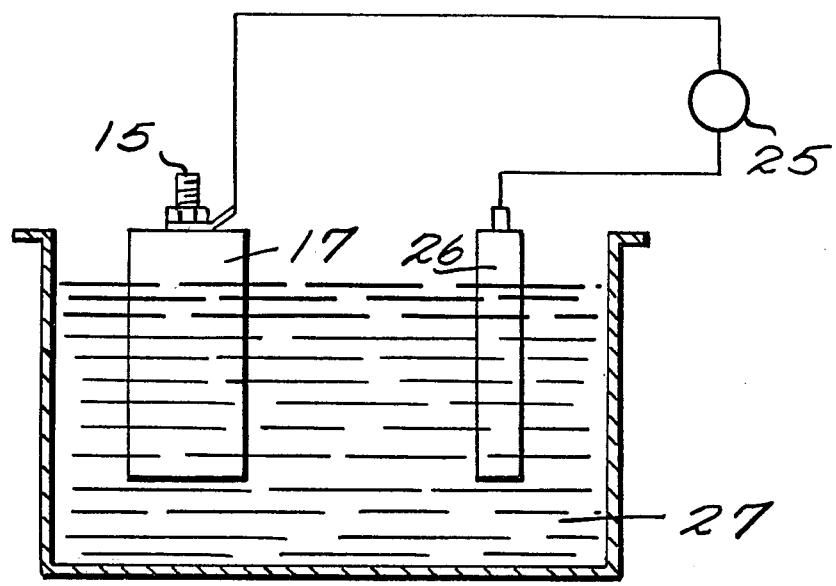
FIG. 4 shows apparatus for determining the concentration of selected ions using the ion sensitive electrode of FIG. 1.

In operation, (see FIG. 4) a potential measuring device 25 of the kind conventionally used with ion-sensitive electrodes is connected between the studding 15 and a reference electrode 26, the active part of the electrode of FIG. 1 is immersed in the electrolyte of interest, and this electrolyte is connected in one of the conventional ways to the reference electrode.

The high ionic mobility of the β alumina 10 allows, in this case, sodium ions to travel through the β alumina to the sodium mercury amalgam 11 and the alumina can thus be considered as a solid extension of the electrolyte. The reversible reaction between metallic sodium and sodium ions which takes place at the interface between the β alumina and the amalgam requires electrons and gives rise in the usual way to a potential on the platinum layer 13, the magnitude of this potential depending on the concentration of sodium ions in the electrolyte.

Figure 2:
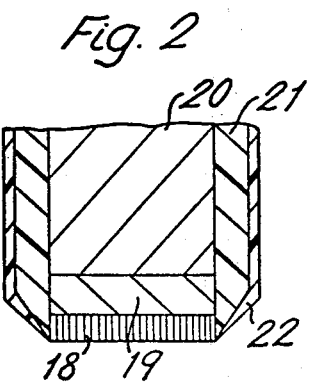
FIG. 2 is a cross-section through part of an ion-sensitive electrode having a β alumina member protecting a tungsten bronze member.

The electrode of FIG. 1 is suitable for the aqueous electrolytes which without the β alumina layer 10 would attack the sodium mercury amalgam. An electrode suitable for use for example in a fused salt electrolyte is shown in FIG. 2. A lithium β alumina layer 18 protects a lithium tungsten bronze member 19. The layer 18 and the member 19 are fixed to a metallic bar 20, for example copper by means of an araldite layer 21. A heat shrunk PTFE sleeve 22 protects the outside of the electrode. As before the β alumina acts a solid extension of the electrolyte and a reversible reaction involving the lithium ions takes place within the tungsten bronze. The high ionic mobility of this material and the lattice defects allow ions to move within the tungsten bronze and alloy ion exchange involving lithium cations and electrons to occur within, or at the surface of the tungsten bronze. Potential measurements giving an indication of ion concentration of lithium are made in the conventional way with the metal bar 20 coupled to one terminal of the potential measuring device which has a reference electrode connected to its other terminal.

Figure 3:
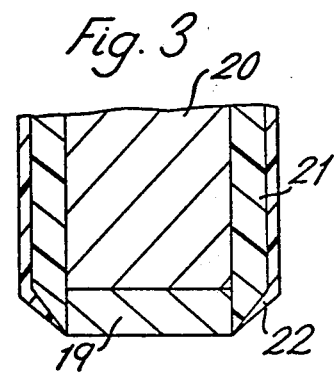
FIG. 3 shows a cross-section through a third electrode according to the invention which uses a tungsten bronze member as the ion-sensitive member.

The electrode shown in FIG. 3 is for use in an aqueous electrolyte and therefore does not require a protective layer of β alumina. Apart from the absence of this layer construction is similar to that of FIG. 2 with a tungsten bronze member 19 the bar 20 for electrical contact purposes, araldite 21 and a PTFE sleeve 22. The type of tungsten bronze used depends, of course, on the ion to be detected. Suitable tungsten bronzes may be prepared, as mentioned above, when some of these ions wholly or partly replace the sodium in sodium tungsten bronze forming the starting point for these materials.

For electrodes of the type shown in FIGS. 2 and 3 which are sensitive to Na+ ions, sodium tungsten bronze is used as the tungsten bronze 19. The ionic interaction which then takes place and gives rise to the potentials measured is:

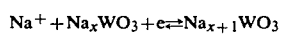

$$Na^+ + Na_xWO_3 + e \rightleftharpoons Na_{x+1}WO_3$$

This interaction is possible because Na+ ions and electrons (e) are able to move freely through the tungsten bronze since its structure provides high ionic mobility.

We claim:
1. An ion-sensitive electrode for determining the concentration of selected monovalent cations in an electrolyte, comprising
   a first member, which includes a β-alumina, for contacting an electrolyte,
   a second member in contact with the first member and comprising a solid mercury amalgam,
   means for making electrical contact with the solid mercury amalgam, and insulating means distinct from the first member, surrounding the second member and the contact means, and construted to form an elongate container shielding both the second member and the contact means from an electrolyte when the electrode is in operation allowing the first member to contact the said electrolyte, the second member being isolated from the electrolyte by being entirely enclosed by an enclosure comprising the insulating means and the first member, and both the β-alumina and the said solid mercury amalgam containing cations selected from the group consisting of Na, K, Rb, Li, Tl, Ag, Cu, NO, Cs and NH₄, allowing the electrode to be used for determining the concentrartion of said cations in an electrolyte.

2. Apparatus for determining the concentration of monovalent cations in an electrolyte, comprising an ion-sensitive electrode, a reference electrode and potential measuring means coupled between the said electrodes, wherein the ion-sensitive electrode includes:

a first member comprising a β-alumina containing cations of a predetermined type and selected from the group consisting of Na, K, Rb, Li, Tl, Ag, Cu, NO, Cs and NH₄, the β-alumina not being capable of substantial chemical reaction with at least one electrolyte, a second member, in contact with the first member comprising a solid mercury amalgam also containing said cations of a predetermined type allowing the electrode to be used for determining the concentration of said cations in an electrolyte, and means for making electrical contact with the solid mercury amalgam, the electrode being so constructed that the second member, but not the first, is isolated in operation from electrolytes, isolation being achieved by entirely enclosing the second member in an enclosure comprising the first member and insulating means.

* * * * *